United States Patent [19]

Magarinos et al.

[11] Patent Number: 4,786,125
[45] Date of Patent: Nov. 22, 1988

[54] OCULAR PROTECTIVE APPARATUS

[75] Inventors: Jose Magarinos; Daniel Coleman, both of Thornwood, N.Y.

[73] Assignee: Farrand Optical Co., Valhalla, N.Y.

[21] Appl. No.: 639,661

[22] Filed: Aug. 13, 1984

Related U.S. Application Data

[63] Continuation-in-part of Ser. No. 525,116, Aug. 22, 1983, abandoned.

[51] Int. Cl.$^4$ .......................... G02B 5/18; G02B 5/32; G02C 7/10; G03H 1/02
[52] U.S. Cl. .................... 350/3.65; 350/3.7; 350/162.17; 351/44
[58] Field of Search .............. 350/3.6, 3.65, 3.7, 350/3.72, 3.77, 162.11, 162.15, 162.17, 162.21, 162.23, 164, 166; 351/44

[56] References Cited

U.S. PATENT DOCUMENTS

| 3,519,339 | 7/1970 | Hutchinson et al. | 350/166 |
| 4,601,533 | 7/1986 | Moss | 350/3.7 |
| 4,637,678 | 1/1987 | Moss et al. | 350/3.7 |

OTHER PUBLICATIONS

Hayford, Michael J., "Holographic Optical Elements," *Photonics Spectra*, vol. 16, #4, Apr. 1982, pp. 77-80.
Rao, S. A., et al, "Holographic Methods for the Fabrication of Various Types of Mirrors," *Rev. Sci. Instrum.* 51(6), Jun. 1980, pp. 809-813.
Johnson, K. C., et al, "Laser Eye Protection," Final Report for 8/7 7-6/79 on Contract N62269-77-R-0307, Naval Air Systems Command, 7/79 (Govt Accession #AD-A112305).

*Primary Examiner*—John K. Corbin
*Assistant Examiner*—David J. Edmondson
*Attorney, Agent, or Firm*—Handal & Morofsky

[57] ABSTRACT

A laser shield (FIG. 3) for providing ocular protection against laser hazards, while still providing high photopic or scotopic transmittance and good color discrimination is disclosed. This laser shield comprises a holographic optical notch filter mirror (102) having an optical surface such that the angle (104) made by an incoming laser beam (114), which is aimed by the pupil of the user, with respect to the normal of the optical surface is less than the corresponding angle (108) made by the same incoming laser beam (114) with respect to the physical surface of the substrate. This decrease in the effective angle of incidence reduces the spectral shift of the notch (which defines the frequency that is reflected), thereby providing increased protection for the same range of angles of incidence. The holographic mirror optical surface formed can be the analog of a conventional spherical, hyperbolic, parabolic, elliptical or other aspheric mirror.

24 Claims, 3 Drawing Sheets

OCULAR PROTECTIVE APPARATUS

CROSS-REFERENCE TO RELATED APPLICATION

This application is a continuation-in-part of abandoned U.S. patent application Ser. No. 525,116 filed Aug. 22, 1983 in the name of Jose Margarinos and Daniel Coleman and entitled Ocular Protection Apparatus.

TECHNICAL FIELD

The present invention is an optical device which may take the form of spectacles, goggles or be incorporated in a visor for providing ocular protection against laser hazards, while still providing high transmittance and good color discrimination.

BACKGROUND OF THE INVENTION

The light generated by a laser is usually very directional and propagates for considerable distances with a concentrated light beam intensity. To protect personnel and material from the hazard posed by this concentrated radiation, an appropriate light shield is required. The light shield, if it is used for eye wear or in the optical path of optical instruments, should not prevent radiation, which is outside the spectral emission band of the laser, from being transmitted.

Also, the light shield should not substantially color distort or attenuate the view of the outside world as seen by the observer from a position behind the shield.

Because the eye is the structure most sensitive to damage from laser radiation, the standards of hazard protection based on safe levels for the eye can also be applied to the rest of the human body and to most optical instrumentation. Whether the laser beam would enter the eye directly or indirectly by way of reflection, the eye must be protected by proper attenuation of the laser intensity.

In accordance with the invention, a holographic optical notch filter (reflection grating) which is an analog of a mirror may be used to provide such protection. These filters have narrow bandwidths, reflecting wavelengths in the notch and passing all other frequencies. Depending on the notch, the range of frequency that is reflected will shift as the angle of incidence of the incident light changes. The notch must therefore be widened as the range of angles of incidence widens in order to consistently reflect a particular wavelength. Otherwise, a beam entering at a particular angle of incidence would not be reflected, whereas a beam entering normal to the filter would be reflected.

SUMMARY OF THE INVENTION

The physical law governing the bending or focusing of light rays by a volume phase grating is expressed by Bragg's law:

$$2nd \sin \theta = \lambda$$

where n is the index of refraction, d is the spacing between the lines or planes in the grating, $\theta$ is the angle at which maximum diffraction occurs and $\lambda$ is the wavelength of light. Using Bragg's law, one may calculate the spectral shift of the wavelength of the notch filter. For example, if $n=1.5$ and the angle of incidence $i=30°$, a notch filter with a center frequency at 532 nm will shift its center frequency to 501.5 nm. Thus, the notch needs to be wider than $532 - 501.5 = 30.5$ nm in order to reflect (reject) an incident beam throughout a given range of angles of incidence, i.e., 0° to 30°. Notches with wider bandwidths have the disadvantage that they block not only the specific frequency that is to be protected against, but also an unnecessarily large range of other frequencies as well. In the particular case of the human eye, the colors of the outside world are easily distorted and the amount of light reaching the eye is reduced. Therefore, the possibility of reduced photopic transmittance and reduced color discrimination exists.

In accordance with the present invention, a spectacle shield incorporating a spherical holographic mirror notch filter is employed on the theory that a spherical mirror surface is more likely to present a normal surface to harmful laser beams heading toward the eye. Moreover, the holographic spherical mirror need not have a spherical physical shape, but rather may be flat or of any curvature, with the spherical analog surface being constructed holographically. The diffraction of the light taking place is, in general, independent of the physical shape of the substrate supporting the grating structure, and the normal to the substrate is not necessarily the normal to the holographic mirror. Thus, "curvature" or "curved" as used herein, means any surface, either physical or optical, not uniplanar or flat.

The spherical holographic mirror is concentric with respect to the eye. Thus the angles of incidence of a beam are limited by the aperture (pupil) of the eye, and it is possible to construct a spherical holographic mirror filter which rejects a beam at large angles of incidence (relative to the filter surface), but still operates with smaller angles. In other words, a beam having a particular angle of incidence relative to the filter surface, will have a more normal angle of incidence relative to the hologrpahic mirror. Since the effects of reduced color discrimination and reduced photopic transmittance result from the large angles of incidence relative to the normal of the holographic mirror, the invention leads to enhanced color discrimination and enhanced photopic transmittance. The holographic spherical mirror will have an improved field of view coverage as compared with a conventional holographic notch filter with a holographic plane mirror.

Further in accordance with the present invention, a spectacle shield incorporating an elliptical holographic mirror notch filter may be employed. In accordance with this alternative embodiment, an elliptical holographic mirror has one of its two foci coincident with respect to each eye of the user. With this configuration, light that is incident in a direction toward the pupil of the eye (a focus of the ellipse) will be reflected in a direction opposite to the other eye (the other focus).

BRIEF DESCRIPTION OF THE DRAWINGS

Two ways of carrying out the invention are described in detail below with reference to the drawings which illustrate only two specific embodiments in which.

PREFERRED EMBODIMENT OF THE INVENTION

Figure 1:
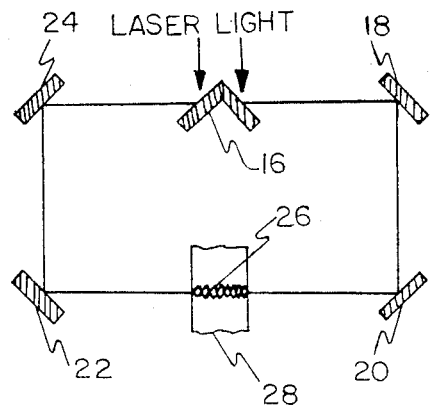
FIG. 1 depicts the standing-wave pattern formed in an emulsion when two coherent plane waves traveling in opposite directions interfere.

A holographic optical element transmits, reflects and focuses light by diffraction. A standing-wave pattern can be recorded in the volume of an emulsion. A standing-wave pattern can be viewed as the interference pattern of two waves moving in opposite directions. If plane-wave laser light is split into two beams by beam-splitting mirror 16 as shown in FIG. 1, and these beams are redirected by mirrors 18, 20, 22 and 24 and caused to be superimposed and to interfere with each other in an emulsion while traveling in opposite directions, a standing-wave pattern 26 is formed in the emulsion. Destructive interference will produce planes of low light intensity in the emulsion and in between there will be planes of strong light intensity. These planar areas of emulsion will be alternately lightly and heavily exposed. The result, following development and fixation of the emulsion 28, will be an interference pattern comprising heavily exposed planes spaced at intervals (for normal incidence) $d = \lambda/(2n \sin \theta)$ (Equation 1) where $\lambda$ is the wavelength of the original laser light. These planes lie within the emulsion. This interference pattern becomes a diffraction grating which will reflect light of a predetermined frequency range upon the proper development of the photographic film.

Figure 2:
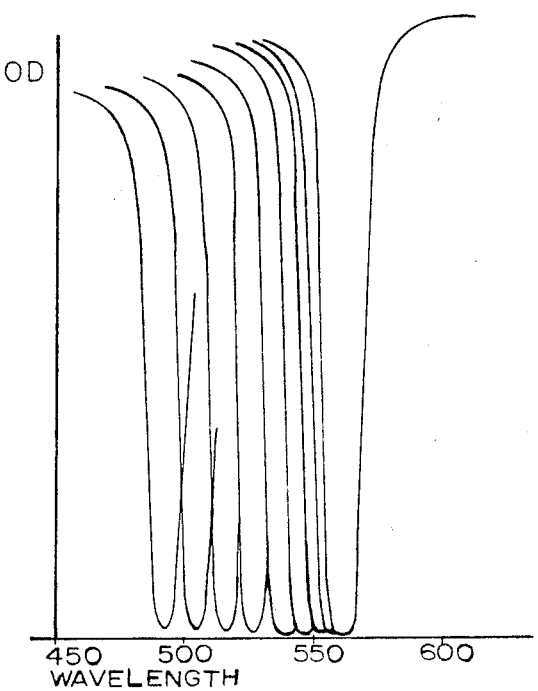
FIG. 2 shows a spectral shift of a 532 nm notch as the angle of incidence of laser beam changes.

The field-of-view coverage or the protection for different angles of incidence of the laser light will usually be related to the bandwidth of the spectrum of light reflected. This narrow range of the spectrum comprising reflected light is called a notch because the shape of the graph of optical density versus wavelength resembles a notch. As noted previously, the notch will shift as the angle of incidence of the laser beam changes. The amount of the spectral shift of the notch corresponding to changes in the angle of incidence changes can be calculated from Equation 1. This shift always takes place toward the lower wavelength region and is a function of the path lengthening between diffraction planes experienced in non-normal incidence. Bandstop curves (in which reflection occurs) for several different angles of incidence showing the spectral shift versus angle of incidence are presented in FIG. 2. The vertical axis corresponds to optical density which is the logarithm of the reciprocal of the transmission (degree of opacity).

If the width of the notch at the points that correspond to the required optical density is larger than the shift due to a particular angle of incidence, then proper coverage will be provided up to the angle of incidence. The bandwidth of the notch may be defined between the half-power points or points with an optical density of $OD = 0.30$ for purposes of this discussion.

The efficiency, spectral bandwidth, and angular response of the holographic optical notch filter can be designed to fulfill particular specifications. These parameters will depend, to a large extent, on the characteristics of the film and on the geometry of the holographic construction-reconstruction. Angular and wavelength selectivities can be obtained as a function of the thickness of the grating.

Multiple spectral notches could provide simultaneous protection from laser beams of more than one wavelength and yet still allow acceptable transmission or view-through. These notches can be located anywhere between the ultraviolet and far infrared spectral regions.

Superimposed notch filters at the same frequency will increase the optical density significantly if they are optically separated (eliminating internal reflections) or with special geometries (which have particular disadvantages). When in optical contact, superimposed notch filters with the same frequency will increase the optical density slightly.

These multiple notches could be registered in the same photographic film but for reasons of diffraction efficiency (optical density), each notch should be registered in a separate film.

As compared to the possiblity of using a simpler holographic plane mirror notch filter to reflect harmful light of known wavelength away from the eye of a user, the present invention utilizes a holographic spherical mirror notch filter in a spectacle configuration that considerably improves (over such a device having a conventional holographic filter) the field of view coverage and simultaneously allows the maximum photopic and/or scotopic transmittance to the eye.

The conventional holographic notch filters are analogs of plane mirrors and have a bandwidth dependent on the desired angular coverage. This is due to the fact that the notch (the frequency that is reflected) will shift with angles of incidence. As noted earlier, the shift for the volume-phase holographic filter is given by Bragg's law.

For example, for $n = 1.5$ and $\lambda = 532$ nm for normal incidence, the notch will shift to 501.5 nm for an angle of incidence of 30°. Considering the use of such a filter in a protective spectacle, the notch in this case needs to be wider than $532 - 501.5 = 30.5$ nm in order to reject the incoming beam throughout the range of angles of incidence from 0° to 30°. Such wide-bandwidth notches will block not only the frequency to be rejected, but many other frequencies as well, thereby distorting the colors of the outside world and reducing the amount of light that reaches the eye.

Figure 3:
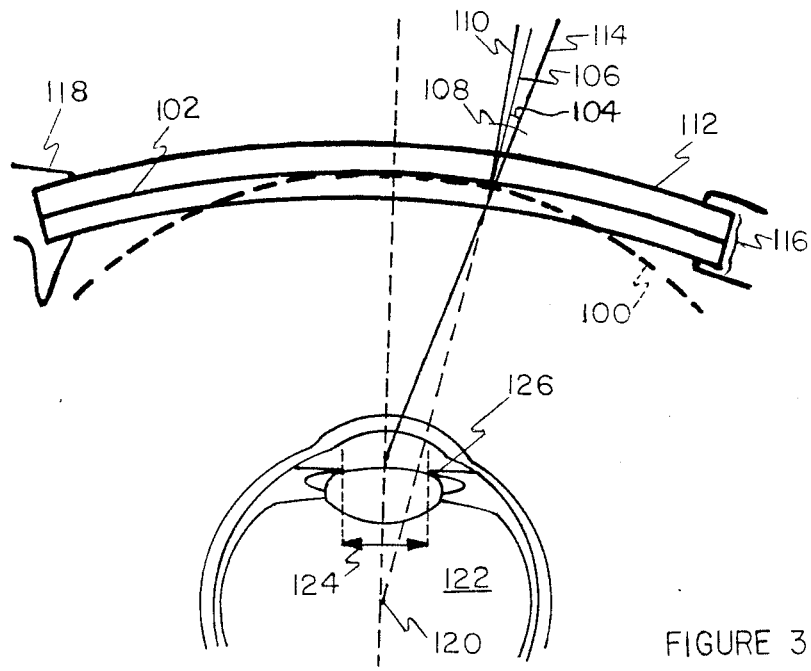
FIG. 3 is a cross-sectional view of a laser shield according to the present invention with the dashed curve indicating the analog surface of a spherical conventional mirror which will work similarly to the holographic spherical substrate mirror embedded in the spectacle substrate.

This disadvantage is obviated by the novel configuration of the present invention. One preferred embodiment of the present invention is a spherical holographic mirror notch filter. This spherical holographic filter is not of a structurally spherical shape and may be perfectly flat or of any curvature, as for example normal spectacle lenses, goggles or a visor. It comprises a substrate with a physically flat or curved surface, and a hologram recorded photographically on a film deposited on the substrate. The hologram has an apparent spherical optical surface that is the analog of a spherical mirror. Referring to FIG. 3, the dashed curve indicates the effective optical surface 100 of the spherical holographic mirror 102. As a result of this curved optical surface 100, the angle of incidence 104 to the normal 106 of the optical surface may be different from the angle of incidence 108 to the normal 110 of the physical surface 112 of the spectacle for an incoming laser beam 114. If the effective optical surface were coincident with the surface of the substrate, both angles of incidence would be the same.

Spectacles 116 are incorporated in the spectacle frame 118 of a user with the holographic spherical mirror positioned in such a manner that its center of curvature is at or close to the center of rotation 120 of the eye 122 of the user. The angles of incidence that must be accounted for are limited by the dimensions of the aperture 124 of the eye defined by its pupil 126, the horizontal and vertical width of the spectacle lens, and the average shape of the users' heads. It is noted that the diagram of FIG. 3 can be used to select optical parameters for mirror 102 for both the horizontal and vertical range of incoming light angles. Angles of incidence greater than these limiting angles determined by the geometry of the eye can be ignored because they pose no hazard to the vision in view of the fact that incoming laer beams will not enter the eye at these larger angles of incidence.

In accordance with the present invention the effective angles of incidence of incoming laser beams are reduced with respect to the normal to the spherical optical surface. In effect, the effective optical surface of the spherical holographical mirror notch filter will reject beams incident at large angles of incidence to the physical surface 112 while operating at smaller effective angles of incidence with respect to the effective optical surface 100. These smaller effective angles of incidence produce a correspondingly smaller spectral shift of the notch. One thus selects a configuration and position for the spherical surface 100 which results in minimal angular deviations with respect to a normal to the optical surface 100 for all incoming laser radiation which is heading toward sensitive portions of the eye. Therefore, the present invention enables the notch filter to provide ocular protection over the same range of angles of incidence as provided by a conventional filter, but the present invention achieves this by means of a notch of narrower bandwidth, thereby improving the overall optical properties of the notch filter (e.g., less color distortion and greater transmittance).

This advantageous protection from laser hazards can be achieved for a plurality of harmful wavelengths by incorporating within lens 102 two or more spheric or conventional holographic mirror notch filters registered in photographic films.

The center of curvature of the spherical mirror need not be at the center of rotation of the eye, but this geometry will, in general, be the most advantageous. It will be noted that the present invention is not restricted to being a spherical mirror, but could also be a mirror with an effective optical surface of any curvature, especially hyperbolic, parabolic, or elliptical. In the case of such a conic section, the geometrical focus of the section would be positioned to coincide with the center of rotation of the eye. The common characteristics of the mirror-like effective optical surface is that the angle made by an incoming laser beam with respect to the normal of the effective optical surface is less than the corresponding angle made by the same incoming laser beam with respect to the physical surface of the spectacle.

The bandwidth (BW) is a trade-off between transmission outside the notch, the field of view coverage, and the optical density. For eye protection and photopic transmission, a 532 nm notch with BW=25 nm will allow a transmission of approximately 80%, and with a BW=40 nm, a transmission of approximately 65% (ignoring substrate absorption and reflections). The field of view coverage (assuming the 532 nm laser wavelength at the low wavelength side of the notch and a moderate optical density of OD=3 to 4) will be approximately 30° for BW=20 nm, 40° for BW=30 nm, and 60° for BW=50 nm. At the center of the notch OD=3 for BW=20 nm, OD=4 for BW=30 nm, OD=5 for BW 35 nm, etc.

The transmission outside the notch is directly related to the bandwidth and to the absorption and reflection of the substrate. For eye and instrumentation protection the transmission outside the notches can attain values larger than 90% when anti-reflection coated glass is used on the substrate.

Figure 4:
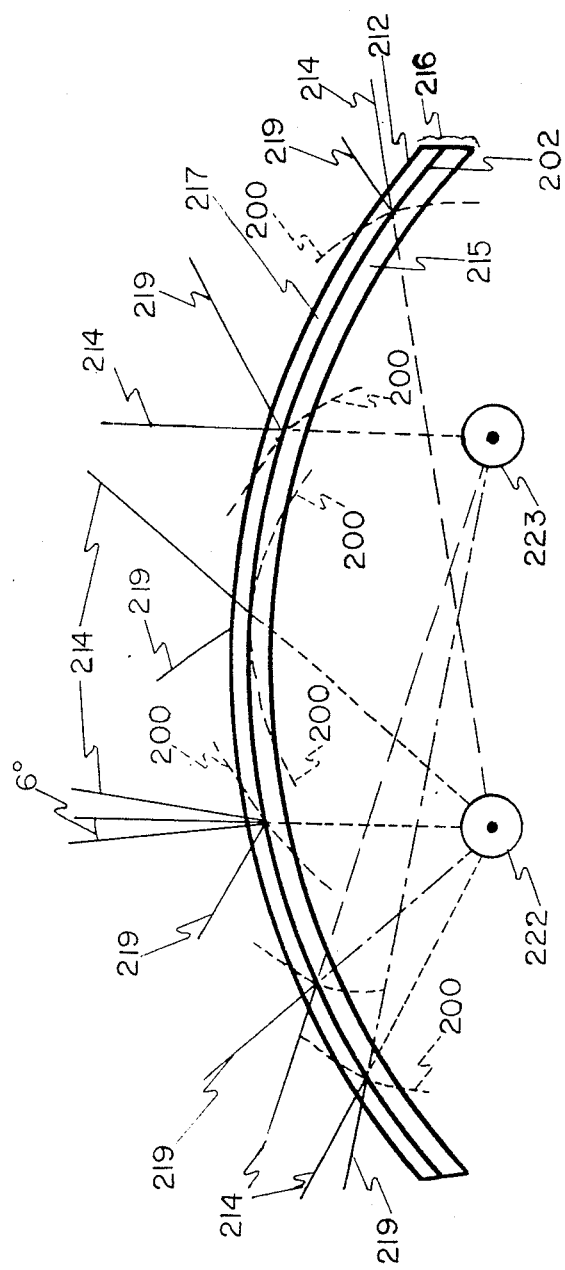
FIG. 4 is a cross-sectional view of a laser shield according to the present invention with the lines passing through the substrate representing a multiplicity of ellipsoidal mirrors which are equivalent to the holographic ellipsoidal mirror embedded in the spectacle substrate.
Figure 5:
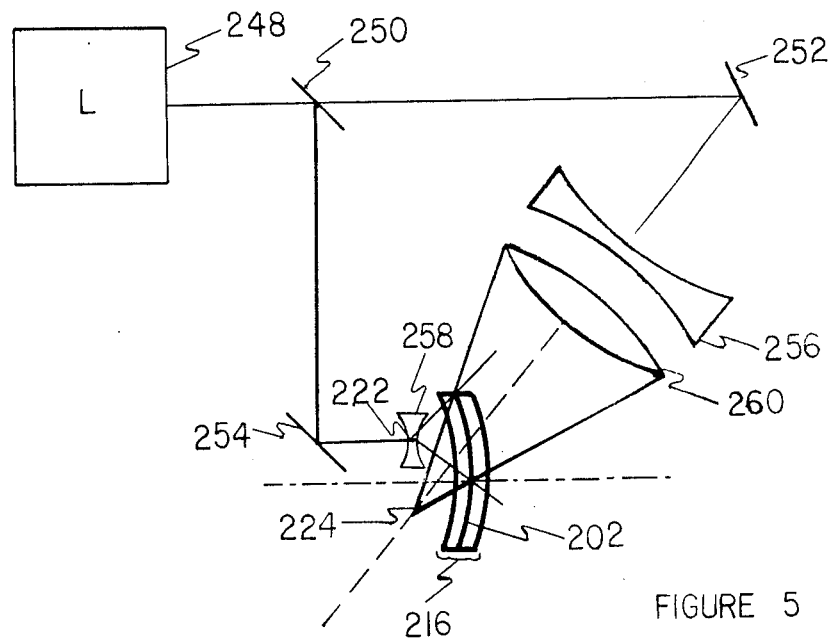
FIG. 5 depicts the exposure of half of an elliptical holographic filter of the type illustrated in FIG. 4.

Referring to FIGS. 4 and 5, another embodiment of the present invention particularly useful to protect the eyes of a user and having an optically elliptical holographic mirror notch filter is illustrated. Similarly, this filter is not of a physically elliptical shape but may be of any curvature. It comprises a hologram recorded photographically in a film 202 deposited on a transparent substrate 215 and protected by a transparent shield 217 of goggle 216. The hologram in film 202 will be optically equivalent to a multiplicity of superimposed ellipsoidal mirrors 200 all of which have their foci at a location approximately the same as the center of rotation of each eye 222 and 223 (FIG. 4).

When the hologram is working as a rejection notch filter, any light ray 214 that is incident in the direction of one focus will be reflected opposite the direction of the other focus by the optical ellipsoidal mirror registered holographically in film 202 and will appear as a reflected ray 219.

Figure 6:
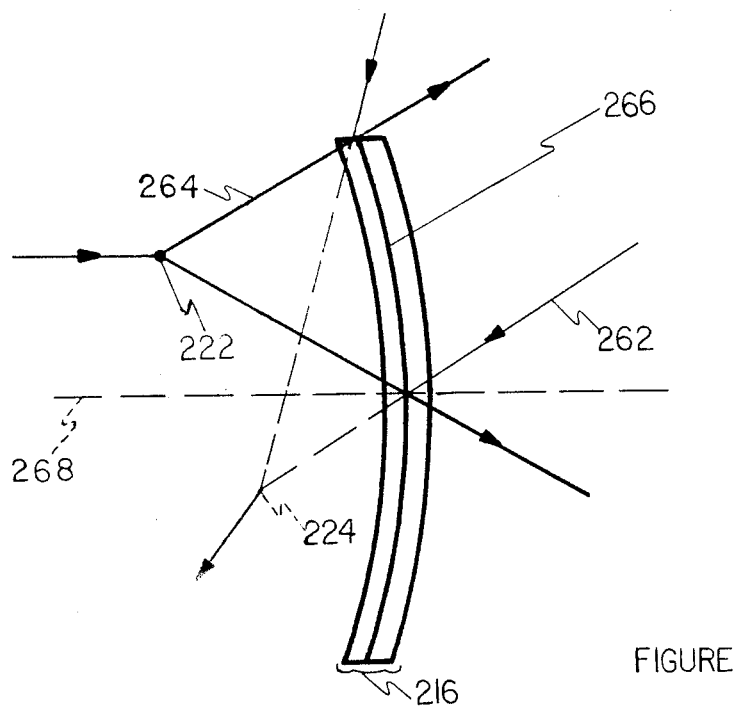
FIG. 6 shows the interference region generated by two oppositely moving light sources.

Th holographic filter of FIG. 4 is made by the interference of two coherent wavefronts as shown in FIGS. 5 and 6. The output of a laser light 248 is split into two beams by a beam-splitting mirror 250. These beams are redirected by a pair of mirrors 252 and 254 and caused to interfere with each other on a photographic surface 202 while traveling in opposite directions as shown. One beam is directed through a first concave or negative lens 258 to produce a diverging waveform 264 (FIG. 6), which diverges from one focus 222 of the ellipsoid. The other beam is directed through a second concave lens 256 and through convex or positive lens 260 to produce a waveform 262 which converges to a second focus 224 of the ellipsoid. A standard wave pattern 266 is thus formed in the emulsion of film 202.

With the process described above it is not practical to cover the total aperture of the lens of the spectacle with one exposure. Thus the hologram is advantageously produced multiply exposing different parts of film 202, illuminating only half of film 202 (in FIG. 6 the half above the centerline 268, of the goggle) and then translating the goggle while holding the light sources constant and exposing the other half of film 202.

With the elliptical mirror notch filter goggle configuration, angles of incidence with respect to one eye as large as 85° and a total angle of 165° for both eyes are covered at the expense of a maximum frequency shift that would correspond to 6° on a planar notch filter. The value of the spectral shift is about 23 nm and will require a notch bandwidth of about 40 nm with which will be obtained a photopic transmittance larger than 65%.

While only two illustrative embodiments of the invention have been described, it is, of course, understood that various modifications will be obvious to those of ordinary skill in the art. Such modifications are within the spirit and scope of the invention which is limited and defined only by the appended claims.

We claim:

1. A light shield for protecting against light of a given wavelength comprising:
   (a) a substrate having a physical configuration defining a first shape;
   (b) a first layer disposed on said substrate;
   (c) a diffractive array being disposed in said first layer, said diffractive array forming a filter which reflects light having a wavelength at or close to said given wavelength, said filter exhibiting reflective characteristics along a curved optical surface defining a second shape, said second shape being positioned, dimensioned and configured with respect to said first shape in such a manner that the angle made by an incident light beam travelling toward an element to be protected with respect to the normal to said second shape is less than the corresponding angle made by said incident light beam with respect to the normal to said first shape at the point of incidence to said first shape; and
   (d) support means for supporting said substrate in front of an element to be protected.

2. A shield as in claim 1, wherein said substrate is transparent.

3. A shield according to claim 2, wherein said second shape defines a substantially spherical optical surface.

4. A shield according to claim 3, wherein said support means supports the substrate in front of the eye of a user and said spherical optical surface is positioned concentric with the eye of the user.

5. A shield according to claim 2, wherein said second shape defines an aspheric optical surface.

6. A shield according to claim 5, wherein said aspheric optical surface is positioned in front of the eye such that the geometrical focus of said aspheric optical surface is substantially coincident with the center of rotation of said eye.

7. A shield according to claim 2, wherein said substrate is made of glass.

8. A shield according to claim 2, wherein said substrate is curved and made of plastic.

9. A shield according to claim 2, wherein said element to be protected receives light through an aperture of an iris and wherein said first layer reflects a predetermined proportion of the radiation of an incident laser beam of predetermined wavelength over a predetermined range of angles of incidence, said range of angles including all angles at which incoming laser beams are headed into the aperture of the iris of said element to be protected.

10. A shield according to claim 9, wherein said second shape defines a substantially elliptical optical surface.

11. A shield according to claim 10, wherein said support means supports the substrate in front of the eyes of the user and said elliptical optical surface is positioned such that at least one eye of the user coincides with a focus of a surface.

12. A shield according to claim 8, wherein said second shape defines a spherical optical surface.

13. A shield according to claim 12, wherein said support means supports the substrate in front of the eye of a user and said spherical optical surface is positioned concentric with the eye of a user.

14. A shield according to claim 9, wherein said second shape defines an aspheric optical surface.

15. A shield according to claim 9, wherein said substrate is curved and made of plastic.

16. A shield as in claim 9, wherein said lattice is an interference pattern in a photosensitive film.

17. A shield as in claim 2, wherein said diffractive array is an interference pattern.

18. A shield according to claim 2, wherein said second shape defines a substantially elliptical optical surface.

19. A shield according to claim 18, wherein said support means supports said substrate in front of the eyes of a user and said substantially elliptical optical surface is positioned such that at least one eye of the user coincides with a focus of a surface.

20. A shield as in claim 2, wherein said substrate is mounted within an eyeglass frame.

21. A shield as in claim 2, wherein an additional layer containing a diffractive array is disposed on said substrate.

22. A light shield for protecting against light of given wavelength comprising:
   (a) a transparent substrate having a physical configuration defining a first shape;
   (b) a first layer disposed on said substrate;
   (c) a diffractive array being disposed in said first layer, said diffractive array forming a filter which reflects light having said given wavelength, said filter exhibiting reflective characteristics along a curved optical surface defining a second shape, said second shape having a pair of focal points and being positioned, dimensioned and configured with respect to said first shape in such a manner that incident light beams heading toward one of said focal points is reflected in the direction away from the other of said focal points; and
   (d) support means for supporting said substrate in front of elements to be protected.

23. A shield according to claim 21, wherein said second shape defines a substantially elliptical optical surface.

24. A shield according to claim 23, wherein said support means supports the substrate in front of the eyes of a user and said substantially elliptical optical surface is positioned such that at least one focus of the surface is substantially coincident with each eye of the user.

* * * * *